United States Patent [19]

Barfurth et al.

[11] Patent Number: 4,647,680

[45] Date of Patent: Mar. 3, 1987

[54] WATER-SOLUBLE TITANIUM ACETYLACETONATES

[75] Inventors: Dieter Barfurth, Troisdorf-Spich; Heinz Nestler, Troisdorf-Eschmar, both of Fed. Rep. of Germany

[73] Assignee: Dynamit Nobel AG, Cologne, Fed. Rep. of Germany

[21] Appl. No.: 658,477

[22] Filed: Oct. 9, 1984

[30] Foreign Application Priority Data

Oct. 12, 1983 [DE] Fed. Rep. of Germany ....... 3337100

[51] Int. Cl.$^4$ .............................................. C07F 7/28
[52] U.S. Cl. .................................. 556/40; 427/126.1; 502/171
[58] Field of Search .......................... 260/429.5, 429 J; 556/40

[56] References Cited

U.S. PATENT DOCUMENTS

| | | | |
|---|---|---|---|
| 3,002,854 | 10/1961 | Brill | 260/429.5 X |
| 3,004,863 | 10/1961 | Gray et al. | 260/429.5 X |
| 3,006,941 | 10/1961 | Mudrak et al. | 260/429.5 X |
| 3,017,282 | 1/1962 | Brill | 260/429.5 X |
| 3,157,661 | 11/1964 | Gray | 260/429.5 X |
| 3,387,994 | 6/1968 | Dunton, III et al. | 260/429.5 X |
| 3,856,839 | 12/1974 | Smith et al. | 260/429.5 |
| 3,946,057 | 3/1976 | Reedy | 260/429.3 X |
| 4,313,851 | 2/1982 | Barfurth et al. | 260/429 R |
| 4,438,039 | 3/1984 | Beers et al. | 260/429.5 |
| 4,478,755 | 10/1984 | Robbins | 260/429.5 |
| 4,551,544 | 11/1985 | Robbins | 556/40 |

FOREIGN PATENT DOCUMENTS

| | | | |
|---|---|---|---|
| 0109014 | 5/1984 | European Pat. Off. | 260/429.5 |
| 734113 | 7/1955 | United Kingdom | 260/429.5 |

*Primary Examiner*—Helen M. S. Sneed
*Attorney, Agent, or Firm*—Felfe & Lynch

[57] ABSTRACT

The present invention relates to new titanium acetylacetonates. The new compounds contain one or two glycol ether groups bound to the central titanium atom. Their solutions in glycol ethers yield, after dilution with water down to chelate contents as low as 1 percent by weight, stable solutions which, even after several months of standing, display neither precipitation nor turbidity.

16 Claims, No Drawings

WATER-SOLUBLE TITANIUM ACETYLACETONATES

BACKGROUND OF THE INVENTION

The subject matter of the present invention is titanium(IV) dialkoxy-bis-acetylacetonates which are soluble in water or whose solutions are miscible with water without incurring degradation.

It is known to use titanium chelates, especially titanium(IV) bis-acetylacetonate, as catalysts, crosslinking agents or coating materials. In contrast to the use of alkyl titanates, it is possible to operate in the presence of water, since the alcoholic solutions of titanium(IV) dialkoxybis-acetylacetonates used in practice are compatible with water. These solutions are generally prepared by the reaction of one mole of a titanic acid tetraalkyl ester, especially tetraisopropyltitanate, with two moles of acetylacetone; that two moles of alcohol that are liberated in the reaction are not distilled away but serve as solvent for the reagent, which is also known as titanium acetylacetonate. Accordingly, the common commercial solutions of titanium acetylacetonate are generally about 75% solutions of this chelate in the alcohol corresponding to the alkoxy group.

In the fields in which titanium acetylacetonates are employed, there is an increasing need to use this reagent in low concentrations, chiefly in concentrations of less than 5%, and to replace the organic solvent largely with water.

The obvious solution of this requirement, namely to dilute the above-named alcoholic solutions of titanium acetylacetonate in water, runs up against the following difficulty: If these alcoholic solutions are simply diluted with water, precipitates form. To prevent the occurrence of such precipitation, the proposal has already been made to add an equal amount by weight of 10% acetic acid to the solution before adding the water, and then to add 13 times the amount of a 1:1 mixture of isopropanol and water, and only then to dilute the solution with water. Other proposals suggest either first to add twice the amount of methyl ethyl ketone and then stir the water in slowly or to add the water in the form of a mixture of 7 parts water and 3 parts isopropanol. All of these proposals are either too costly and time-consuming, or they increase the organic solvent content, or they do not provide a satisfactory solution of the problem.

The problem therefore existed of preparing titanium acetylacetonate solutions which can be diluted to solutions of less than 5% by the simple addition of water, without incurring turbidity in the solutions.

THE INVENTION

As a solution of this problem, titanium(IV) dialkoxy-bisacetylacetonates have been found, which are characterized by the fact that at least one of the alkoxy groups is an alkyl oxyalkylenoxy group or an alkyl oxypolyalkylenoxy group.

The new compounds are water-soluble. Their solutions in glycol ethers and polyglycol ethers can also be diluted with water, and are especially well suited for the production of low-percentage acetylacetonate solutions having contents of the new titanium acetylacetonates under 5 weight-percent. The use of such (poly)-glycolether solutions as starting solutions for the preparation of dilute aqueous titanium(IV) acetylacetonate solutions is especially recommended because these solutions are the direct product of the preparation of the new compounds.

The preparation is generally performed from the known titanium(IV) dialkoxy-bis-acetylacetonates or from their alcoholic solutions. To these is added as much glycol ether or polyglycol ether as is necessary for the establishment of the desired concentration of titanium chelate and for the exchange of one or two alkoxy groups per mole of titanium chelate. Then the mixture is heated to at least 40° C. and the solvent alcohol and the alcohol that has formed is distilled out. The distillation is best performed in vacuo. On account of the boiling point differences between the alcohol and the glycol ethers, this procedure and the separation of the alcohol present no problems.

If only one alkoxy group in the commonly used alcoholic titanium(IV) dialkoxy-bis-acetylacetonate solution (with two moles alcohol per mole titanium comound) is to be exchanged, three moles of alcohol accordingly have to be removed per mole of titanium chelate solution, and if both alkoxy groups are to be exchanged, four moles of alcohol must be removed from the mixture. If it is desired to prepare the new compounds in solvent-free form, then only as many moles glycol ether or polyglycol ether is used in the above procedure as corresponds to the moles bound alcohol that is to be exchanged. The distillation of the alcohol is then continued until both the original bound alcohol as well as the simple alcohol used as solvent has been removed.

For technical, practical purposes, however, the preparation of water-compatible solutions of the new titanium chelate (with two moles alcohol per mole of titanium compound) suffices. Then, again, both the bound alcohol present in the starting product and the simple alcohol contained as solvent are to be distilled out as completely as possible.

The amount of solvent to be used in the glycol ether solutions of the new titanium chelates can vary greatly. It is best to select the amount such that the titanium chelate content of the solutions is more than 50 weight-percent and the viscosity of the solutions obtained is not too high. The preferred range of the solutions is generally between 50 and 75 weight-percent.

The glycol ethers which can be used, both in the form of their alkoxy moiety in the new titanium chelates and in the form of solvents for the new chelates, correspond to the general formula $HO-[A-O]_n-R$, wherein A represents an ethylene or propylene moiety, R represents an alkyl moiety of 1 to 4 carbon atoms and n can assume values between 1 and 8, preferably between 1 and 4. Examples of such glycol ethers are glycol monomethyl ether, glycol monoethyl ether, glycol monoisopropyl ether, glycol monobutyl ether, propylenglycol monomethylether, diglycol monomethyl ether, diglycol monoethyl ether, diglycol monobutyl ether and dipropylenglycol monomethylether. Glycol ether mixtures can also be used, so that different glycol ether moieties can also be contained in the new chelates.

The reaction of the titanium(IV) dialkoxy-bis-acetylacetonates with the glycol ethers can also be performed with the corresponding alkyl glycol carboxylates, which are also referred to as glycol esters. Examples are glycol monomethyl ether acetate and diglycol monobutyl ether acetate. These compounds react with the titanium acetylacetonate with ester exchange. Like the above-named glycol ethers, they can also be used as solvents.

The titanium acetylacetonate which is used preferentially for the preparation of the new compounds and their solutions is diisopropoxy-bis(acetylacetonato)-titanium, which is also referred to as diisopropoxy-bis-(2,4-pentanedionato)titanium(IV). However, other titanium acetylacetonates in which the diisopropoxy group is replaced, for example, by the n-butoxy, n-propoxy, isobutoxy or ethoxy group, and which are dissolved in the alcohols corresponding to the alkoxy group, can be used as starting products.

The titanium chelates of the invention can be used whenever hydrolysis-resistant organic titanates are needed as reactants. They are used to advantage especially where low concentrations of titanate are to be available in aqueous solution for use as coating materials, crosslinking agents or catalysts, as for example for the surface treatment of substrates, for the improvement of the properties of water varnishes on a basis of polyesters, or for the crosslinking of cellulose derivatives and starch derivatives in aqueous solution.

EXAMPLES

EXAMPLE 1

Preparation of bis-2-(2-methoxy-ethoxy)ethoxytitanium-bis-acetylacetonate 242 g of common commercial titanium acetylacetonate (0.5 mol as a 75% solution in isopropanol) is weighed into the one-liter flask of a laboratory rotary vacuum evaporator, and 120 g of methyl diglycol (1 mole of 2-(2-methoxyethoxy)ethanol) is added. Then, beginning at a water bath temperature of 35° C., which is raised in the course of 6 hours to 80° C., and at a reduced pressure of 25 mbar, both the isopropanol present in the starting material and the isopropanol that is formed in the exchange reaction of the titanium acetylacetonate with the methyl diglycol are distilled out. The yield is 119.7 g of isopropanol (99.8% of the theory=120 g, 2 moles). The product thus obtained is a dark red, very fluid liquid of the following characteristics:

Index of refraction $n_D^{20} = 1.5440$.
Viscosity (20° C.)=57.5 mPa.s.
Titanium dioxide content=16.4%.
Solubility: Soluble in isopropanol, methyl ethyl ketone, toluene, or methylene chloride. For example, 10% solutions in these solvents are stable for at least three months.

EXAMPLE 2

Preparation of isopropoxy-2-(2-methoxyethoxy)titanium-bis-acetylacetonate 242 g of common commercial titanium acetylacetonate (0.5 mole as 75% solution in isopropanol) is weighed into the one-liter flask of a laboratory rotary vacuum evaporator, and 60 g of methyl diglycol (0.5 mole, 2-(2-methoxyethoxy)ethanol is added. The distillation of isopropanol is then performed at reduced pressure (approx. 25 mbar) as described in Example 1. 89.6 g of isopropanol is obtained (99.6% of the theory=90 g, 1.5 moles). The product thus obtained is a dark red, very fluid liquid, having the following characteristics:

Titanium dioxide content=18.3%.
Solubility: Soluble in isopropanol, methyl ethyl ketone, toluene or methylene chloride. For example, 10% solutions in these solvents are stable for at least three months.

EXAMPLE 3

Preparation of a 65% solution of the titanium chelate of Example 1 in methyl diglycol 242 g of common commercial titanium acetylacetonate (0.5 mole as 75% solution in isopropanol) is weighed into the one-liter flask of a laboratory rotary vacuum evaporator, and 250 g of methyl diglycol (120 g=1 mole, for the exchange of the isopropoxy groups, 130 g as solvent) is added. Then, as described in Example 1, isopropanol is distilled out at reduced pressure (approx. 25 mbar). 119.5 g of isopropanol is obtained (99.5% of theory=120 g, 2 moles). The product is a dark brown liquid which can be mixed with water in any ratio.

EXAMPLE 4

(Comparative Example)

Preparation of a 75% solution of diisopropoxytitanium-bis-acetylacetonate in methyl diglycol 242 g of common commercial titanium acetylacetonate (0.5 mole as a 75% solution in isopropanol) is weighed into the one-liter flask of a laboratory rotary vacuum evaporator and 60 g of methyl diglycol is added. This amount of methyl diglycol corresponds to the amount of the free isopropanol contained in 242 g of titanium acetylacetonate. At a reduced pressure of 25 mbar and a water bath temperature of 25° C., isopropanol is withdrawn for 6 hours by means of a water-jet pump. Reweighing the flask contents indicates a weight loss of 59.5 g, i.e., 99.2% of the free isopropanol contained in the titanium acetylacetonate has been removed and replaced by methyl diglycol.

EXAMPLE 5

Testing the solubility of the products of Examples 1 to 4 in water in concentrations ranging from 1 to 2.5%

| Product of | Solubility in desalted water at a titanium chelate concentration of | |
|---|---|---|
| | 1% | 2.5% |
| Example 1 | Clear solution | Clear solution |
| Example 2 | Clear solution | Clear solution |
| Example 3 | Clear solution | Clear solution |
| Example 2, diluted with methyl diglycol to 50% | Clear solution | Clear solution |
| Commercial titanium acetylacetonate = 75% solution in isopropanol | Sediment forms immediately | Sediment forms immediately |
| Titanium acetylacetonate, diluted with methyl diglycol to 50% | Slightly turbid solution | Sediment forms immediately |
| Example 4 | Slightly turbid solution | Sediment forms immediately |

EXAMPLE 6

Use of 1 and 2.5% aqueous solutions of the products of Examples 1 and 2 for the modification of the surfaces of metals, plastics, fillers and glass fibers (a) For the surface treatment of sheet aluminum, a 2% solution of the product of Example 1 in water is prepared and an aluminum plate (dimensions: 15×8×0.1 cm) is immersed in it for 30 seconds. After the excess solution has been drained off and the plate has been dried in warm air, there remains on the aluminum a coating which improves the adherence of subsequent varnishing to a degree equal to that obtained by immersing an identical plate in a 2% solution of commercial titanium acetylacetonate in toluene and drying.

(b) The procedure of (a) can be applied to the adhesion-promoting surface treatment of plastics, such as polyethylene or polyester films, filler materials and glass fibers. In these applications, it has formerly been necessary to use combustible or physiologically objectionable organic solvents, or the titanium acetylacetonate has had to be transformed by difficult procedures to an only partially aqueous solution.

It will be understood that the specification and examples are illustrative but not limitative of the present invention and that other embodiments within the spirit and scope will suggest themselves to those skilled in the art.

We claim:

1. A water-soluble titanium (IV) dialkoxybisacetylacetone compound wherein at least one of the alkoxy groups linked to the titanium atom is a radical of an alkyl oxyalkylenoxy or alkyl oxypolyalkylenoxy group of the general formula HO—[A—O]$_n$—R, wherein A is an ethylene or propylene moiety, R is an alkyl moiety of 1 to 4 carbon atoms and n is 1 to 8.

2. The water-soluble compound of claim 1, wherein n is 1 to 4.

3. The water soluble compound of claim 1 designated as isopropoxy-2-(2-methoxyethoxy)ethoxytitanium-bis-acetylacetonate.

4. The water soluble compound of claim 1 designated as bis-2-(2-methoxyethoxy)ethoxytitanium-bis-acetylacetonate.

5. A solution of a compound of claim 1 in glycol ethers or polyglycol ethers of between 10 and 99 weight-percent of the compound.

6. The solution of claim 5, wherein the compound is isopropoxy-2-(2-methoxyethoxy)ethoxytitanium-bis-acetylacetonate.

7. The solution of claim 5, wherein the compound is bis-2-(2-methoxyethoxy)ethoxytitanium-bis-acetylacetonate.

8. The solution of claim 5, further comprising water as additional solvent, and wherein the titanium chelate content in the solution is between 1 and 4 weight-percent.

9. The solution of claim 6, further comprising water as additional solvent, and wherein the titanium chelate content in the solution is between 1 and 4 weight-percent.

10. The solution of claim 7, further comprising water as additional solvent, and wherein the titanium chelate content in the solution is between 1 and 4 weight-percent.

11. A method of preparing the water soluble compound of claim 1 comprising adding glycol ether or polyglycol ether to titanium acetyl acetonate and distilling out, under reduced pressure, the free and the formed alcohol at temperatures up to about 80° C.

12. The method of claim 11, wherein said glycol ethers and polyglycol ethers are of the general formula HO—[A—O]$_n$—R, A represents an ethylene or propylene moiety, R represents an alkyl moiety of 1 to 4 carbon atoms and n is 1 to 8.

13. The method of claim 12, wherein n is 1 to 4.

14. A method of preparing a solution defined in claim 7 comprising adding glycol ether or polyglycol ether to titanium acetyl acetonate and distilling out the free and the formed alcohol at temperatures up to about 80° C. and reduced pressure wherein the glycol ether or polyglycol ether are present in a sufficient excess such that the desired concentration of the solution is obtained after distilling out the alcohol.

15. The method of claim 14 wherein glycol ethers and polyglycol ethers are of the general formula HO—[A—O]$_n$—R, A represents an ethylene or propylene moiety, R represents an alkyl moiety of 1 to 4 carbon atoms and n is 1 to 8.

16. The method of claim 15, wherein n is 1 to 4.

* * * * *